(12) United States Patent
Esaki

(10) Patent No.: US 7,951,443 B2
(45) Date of Patent: May 31, 2011

(54) TAPING TAPE

(75) Inventor: Kenzo Esaki, Nagaokakyo (JP)

(73) Assignee: Esaki Medical Instrument Co., Ltd., Nagaoka-shi (JP)

( * ) Notice: Subject to any disclaimer, the term of this patent is extended or adjusted under 35 U.S.C. 154(b) by 714 days.

(21) Appl. No.: 11/921,163

(22) PCT Filed: May 24, 2006

(86) PCT No.: PCT/JP2006/310341
§ 371 (c)(1),
(2), (4) Date: Nov. 28, 2007

(87) PCT Pub. No.: WO2006/129537
PCT Pub. Date: Dec. 7, 2006

(65) Prior Publication Data
US 2009/0104402 A1   Apr. 23, 2009

(30) Foreign Application Priority Data

May 31, 2005   (JP) .................................. 2005-158561

(51) Int. Cl.
*B32B 3/10* (2006.01)
(52) U.S. Cl. ........ 428/136; 428/131; 428/134; 428/343; 602/59; 602/76; 602/47

(58) Field of Classification Search ................ 602/59, 602/76, 47; 428/131, 134, 136, 343
See application file for complete search history.

(56) References Cited

U.S. PATENT DOCUMENTS 5,947,917 A * 9/1999 Carte et al. .................. 602/52

FOREIGN PATENT DOCUMENTS

| JP | 4-92220 U | 8/1992 |
|----|-----------|--------|
| JP | 2002-35196 A | 2/2002 |
| JP | 2002-233545 A | 8/2002 |
| JP | 3097985 U | 9/2003 |
| JP | 3108052 U | 1/2005 |

* cited by examiner

*Primary Examiner* — Michael C. MIggins
(74) *Attorney, Agent, or Firm* — Kubovcik & Kubovcik

(57) ABSTRACT

A taping tape includes: a base material 12 having elasticity; an adhesive layer attached to one side of the base material 12; and plural slits 14 that are formed along one direction on an inner side of the base material 12 and are arranged parallel to each other. Both side edge portions 12a and 12b of the base material 12 in the vicinities of end portions of the slits 14 are formed obliquely to each other towards a longitudinal direction center of the base material 12 from the vicinities of the end portions of the slits 14 to base material end portions 12c and 12d positioned on extensions of the slits 14. The end portions of the slits 14 curve towards the center of the base material 12 along the side edge portions 12a and 12b.

3 Claims, 4 Drawing Sheets

TAPING TAPE

TECHNICAL FIELD

The present invention relates to taping tape that is used to alleviate muscle and joint pain and to prevent disability.

BACKGROUND ART

Conventionally, various methods of taping have been performed to alleviate muscle pain. For example, there is a method of surrounding, while supporting, an area where a muscle hurts so that the pain does not spread. As taping tape suited for this, as shown in FIG. 5, there is taping tape that is created by a base material capable of stretching and contracting vertically and horizontally and is formed as a result of a band of a certain width being cut into a predetermined length. An adhesive layer coated with an adhesive is disposed on one side of the base material, and a peel-away sheet is attached to the outside of the adhesive layer. Additionally, slits are disposed in the base material parallel to the longitudinal direction of the base material. The slits are disposed such that a plural number of slits of the same length are arranged in a direction orthogonal to the longitudinal direction of the base material. Additionally, portions between each pair of slits become long and narrow strips. The slits stop at positions a predetermined length away from both longitudinal direction end portions of the base material, and both end portions of the base material are cut and left to become connecting portions that interconnect the plural strips.

Next, the method of using this taping tape will be described on the basis of FIG. 5. In this case, treatment of shoulder joint inflammation or shoulder pain is performed. Taping is administered to a patient in a natural posture where the patient is seated in a chair. First, the peel-away sheet attached to taping tape 1 is peeled away to expose the adhesive layer, and the taping tape 1 is adhered from the center of the trapezius muscle (the muscle running from the neck to the shoulder and the back) to the deltoid muscle. Next, strips 2 are spread apart outward in intervals about the size of a middle finger so as to surround the area of the shoulder.

However, this taping tape 1 has the problem that, when the peel-away sheet is peeled away and the taping tape is adhered with the adhesive surface facing the body, the plural strips 2 move away from each other and become tangled such that the taping tape 1 loses its shape, and adhesion to the body becomes difficult. Further, sometimes the strips 2 also become twisted such that the adhesive layers stick to each other and handling becomes complicated.

In order to solve this, there has been the therapeutic tape disclosed in Patent Document 1 below. This therapeutic tape is one where a connecting member is attached, such that it may be freely separated and so as to straddle plural slits, to the opposite side of the adhesive surface adhered to the body. The connecting member is a sheet member or a linear member.

Patent Document 1: JP-A-2002-238944

DISCLOSURE OF THE INVENTION

Problem that the Invention is to Solve

However, the above-described conventional taping tape 1 is created by cutting the base material into strips that are rectangles which are long in one direction; thus, as shown in FIG. 5, when the strips are spread apart and adhered to the body, the base end portions of the strips 2 become bent and cannot be absorbed by the elasticity of the base material, and sometimes wrinkles 3 form or the taping tape 1 peels away and rises up from the body, so the taping tape 1 has not been able to be reliably applied. When a person puts clothes on over the taping tape 1 in a state where the taping tape 1 has risen up from the body in this manner, concavo-convexities arise in the surface and strike the body, so there has been a feeling of discomfort. Further, in a state where the strips 2 have peeled away, the effect of relieving pain becomes lower, so a sufficient pain preventing effect has been unable to be obtained.

This invention has been made in view of the above-described problem in the prior art, and it is an object thereof to provide taping tape that is adhered in a state where it reliably closely contacts the body and with which the strips can be spread apart in a free shape corresponding to the shape of the affected area or application site.

Means for Solving the Problem

The present invention is a taping tape including: a base material having elasticity; an adhesive layer formed on one side of the base material; and plural slits that are formed along one direction on an inner side of the base material and are arranged parallel to each other, wherein both side edge portions of the base material in the vicinities of end portions of the slits are formed obliquely to each other towards a longitudinal direction center of the base material from the vicinities of the end portions of the slits to base material end portions positioned on extensions of the slits, and the end portions of the slits curve towards the center of the base material along the side edge portions.

Moreover, both side edge portions of the base material along the slits are formed in curved lines that swell outward, and the slits are formed along the longitudinal direction of the base material and are formed in curved lines along the side edge portions.

Short cuts are formed at predetermined intervals in the base material at right angles with respect to the slits. A knitted structure such as Russell knitted fabric is suited for the structure.

EFFECTS OF THE INVENTION

The taping tape of the present invention is taping tape that is adhered so as to reliably closely contact the body and with which the strips can be spread apart in a free shape corresponding to the shape of the affected area or application site and in which it is difficult for wrinkles to form. Thus, the taping tape can alleviate muscle pain in the site to which taping has been administered and can effectively prevent disability.

DESCRIPTION OF THE REFERENCE NUMERALS

10 Taping Tape
12 Base Material 12a, 12b Side Edge Portions
12c, 12d Base Material End Portions
14 Slits
16 Strips
18 Connecting Portions

BEST MODES FOR IMPLEMENTING THE INVENTION

Figure 1:
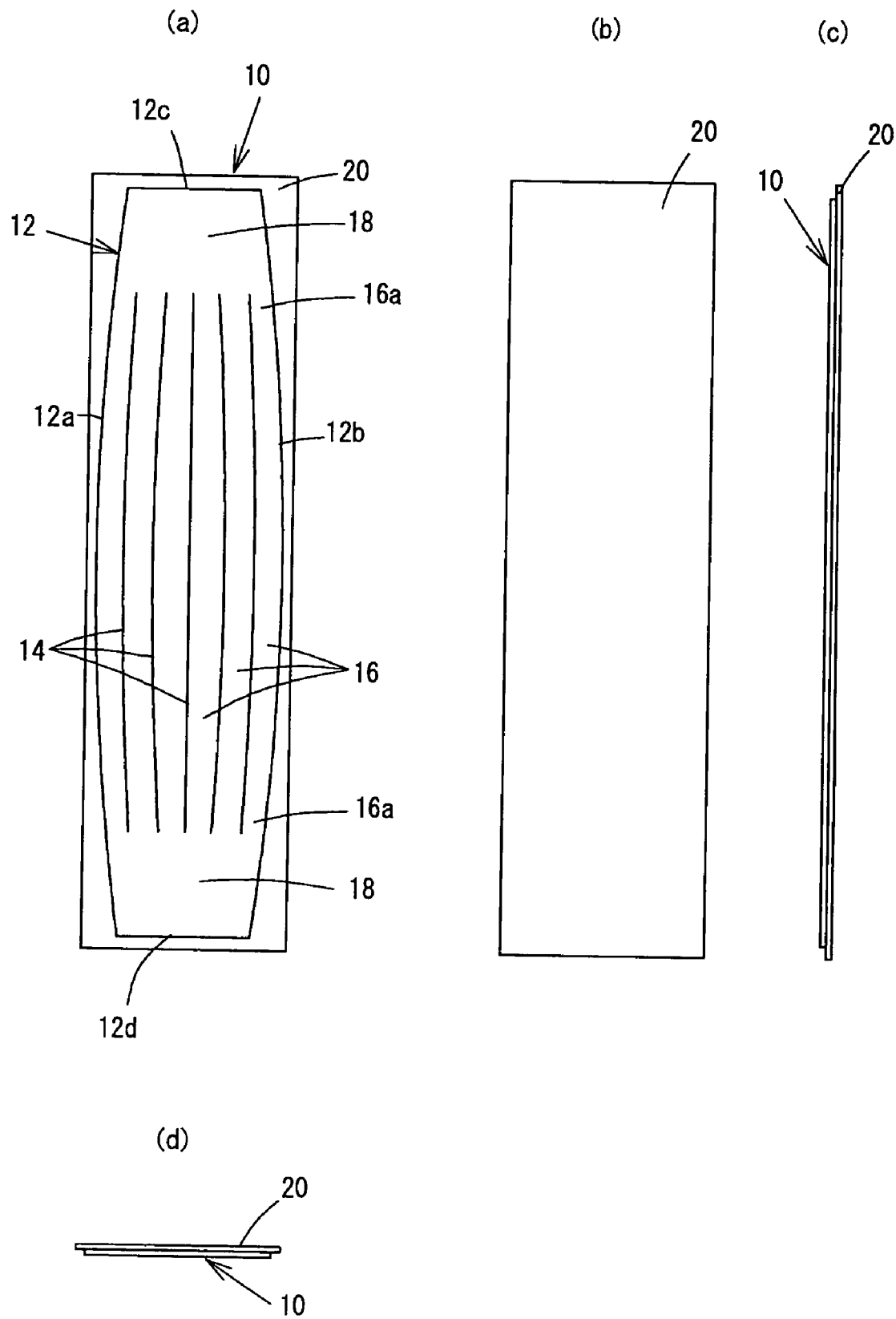
[FIG. 1] (a) a front view, (b) a rear view, (c) a right side view and (d) a bottom view of a state where taping tape of an embodiment of this invention is adhered to a peel-away sheet.

Below, embodiments of this invention will be described on the basis of the drawings. FIG. 1 shows taping tape of an embodiment of this invention. A taping tape 10 of this embodiment is a textile or the like having flexibility and is created by a base material 12 having elasticity averagely in the two directions of vertical and horizontal. The elasticity of the base material 12 is created such that it is close to that of the skin, ligaments and muscles of a human body and with which is obtained a soft, fit feeling and a moderate fixed feeling on an area where there is pain. For example, a nylon material is used for the material of the base material 12. A nylon material is resistant to water, has breathability, and controls itching and rashes. A structure resulting from a textile is suited for the structure of the base material 12 in view of elasticity.

The base material 12 is cut into a substantial band-like shape that is long in one direction, and a pair of side edge portions 12a and 12b along the longitudinal direction are formed in curved lines whose central vicinities swell outward. Thus, the vicinity in the center of the longitudinal direction central axis of the base material 12 is fat. A pair of base material end portions 12c and 12d positioned on the longitudinal direction end portions of the base material 12 are formed in straight lines that are substantially orthogonal to the longitudinal direction.

Five slits 14 that cut the base material 12 are disposed in the base material 12. The slits 14 are formed along the longitudinal direction of the base material 12 and are arranged parallel to each other in a direction orthogonal to the longitudinal direction of the base material 12. The single slit 14 in the center is a straight line that is parallel to the longitudinal direction of the base material 12, and the two slits 14 positioned between the central slit 14 and the side end portion 12a are formed in curved lines along the side edge portion 12a. Further, the two slits 14 positioned between the central slit 14 and the side edge portion 12b on the opposite side are formed in curved lines along the side edge portion 12b. Both end portions of each of the five slits 14 are positioned a predetermined length on the inner side of the base material end portions 12c and 12d of the base material 12. Areas between each pair of the slits 14 and also between the slits 14 and the side edge portions 12a and 12b are long and narrow strips 16, and portions in the vicinities of the base material end portions 12c and 12d where the slits 14 are not disposed are connecting portions 18 that interconnect base end portions 16a of the strips 16.

An adhesive is applied to, such that an adhesive layer is disposed on, one side of the base material 12. Further, a peel-away sheet 20 is attached to the outside of the adhesive layer. Cutting and formation of the slits 14 may be performed after the base material 12 is attached to the peel-away sheet 20, so that the slits 14 are also communicably formed in the peel-away sheet 20. An acrylic material having little irritability, for example, is used for the adhesive, and the adhesive has excellent breathability.

Next, the method of using this taping tape 10 will be described. The way the taping tape 10 is applied is simple; for example, the taping tape 10 is applied limited to a place where there is pain. The taping tape 10 utilizes tension in the base material 12, and when the taping tape 10 is to be adhered to the body, it is done so with the body being a natural posture such that the skin, ligaments and muscles do not stretch or contract too much. Further, the taping tape 10 is stretched and adhered to an extent that there is no slack.

Figure 2:
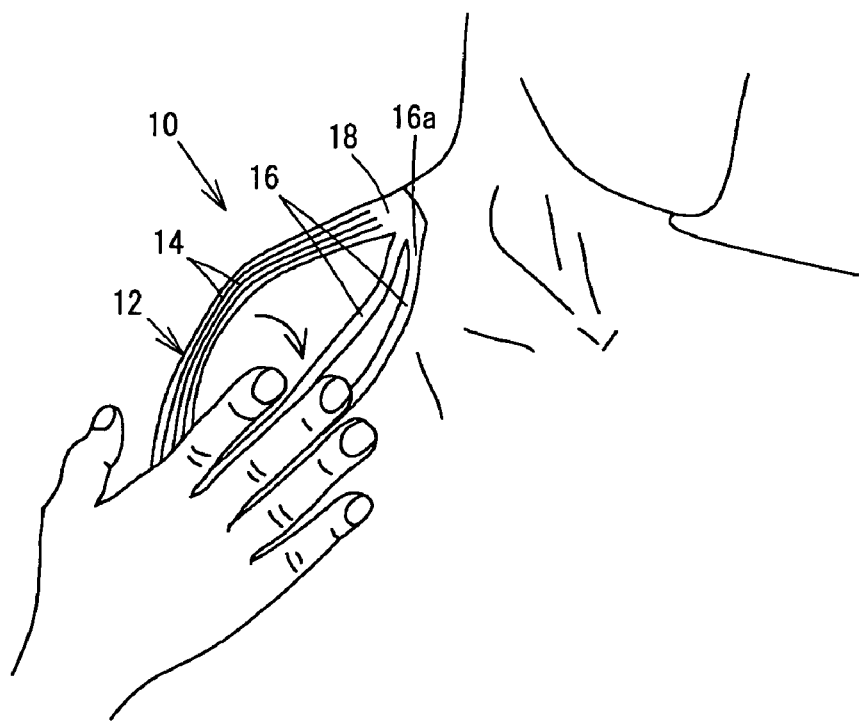
[FIG. 2] A perspective view showing a state where the taping tape of this embodiment is adhered.
Figure 3:
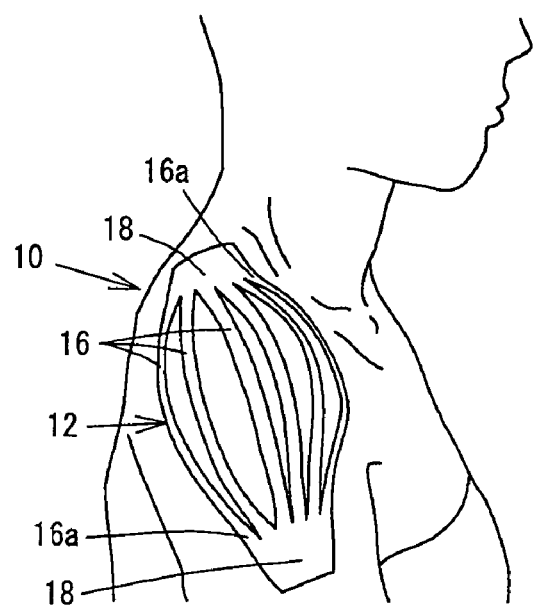
[FIG. 3] A perspective view showing a state where the taping tape of this embodiment is used.

The method of using the taping tape 10 will be specifically described on the basis of FIG. 2 and FIG. 3. In this case, treatment of shoulder joint inflammation and muscle pain is performed. Taping is administered to a patient in a natural posture where the patient is seated in a chair. First, the peel-away sheet is peeled away from the taping tape 10 to expose the adhesive layer, and the taping tape 10 is adhered from the center of the trapezius muscle (the muscle running from the neck to the shoulder and the back) to the deltoid muscle. Next, as shown in FIG. 2, the strips 16 are spread apart in order from the outside in intervals about the size of a middle finger so as to surround the area of the shoulder. FIG. 3 shows a state where all of the strips 16 have been completely spread out.

As for the sites where the taping tape 10 is used, various sites in addition to the shoulder are possible, such as the neck, elbows, hands and fingers, chest, back, abdomen, waist, hip joints, from the buttocks to the thighs, the knees, the lower thigh regions, and the feet. The taping tape 10 is usable on sites where there is pain, on places where pain always emerges whenever one does some kind of exercise, and for emergency treatment after an accident, such as for sprains, bruises, and dislocations. Particularly when the taping tape 10 is used on places where there is pain, the taping tape 10 works extremely well in relation to use in cases where there is acute or chronic pain. In cases of prevention of injury resulting from sports or the like or when pain is severe, the effect of the taping tape is high when two of the taping tapes are adhered such that they intersect each other at an appropriate angle, such as a 90° to 60° angle.

According to the taping tape 10 of this embodiment, the taping tape is adhered in a state where it reliably closely contacts the body, and the strips 16 can be spread apart in a free shape corresponding to the shape of the affected area. Because the plural strips 16 on the outside are disposed such that they curve outward, deformation of the base material 12 does not become large even when the stripes 16 are spread apart to desired positions, and the base end portions of the strips 16 in the vicinities of the connecting portions 18 do not become wrinkled and do not rise and peel away from the body. Thus, the taping tape 10 reliably closely contacts the body so that the effect of relieving muscle pain can be sufficiently obtained. Further, because the taping tape 10 does not wrinkle or rise, there are no concavo-convexities, there is no feeling of discomfort, and it is natural even when one wears clothes over the taping tape 10, and the adhesive layer does not end up sticking to clothes. The way the taping tape 10 is applied is simple, so that anyone can use the taping tape 10. By adhering this taping tape 10 to the body, tense muscles are eased, and the skin, muscles and ligaments are protected. Thus, general muscle balance can be averaged thoroughly and pain can be soothed. Further, because each of the strips 16 contracts towards its center in the longitudinal direction and draws the skin, wrinkles are formed in a corrugated plate manner in the skin and the circulation of lymphatic fluid quickens, so there is also the effect of controlling edema after surgery and edema of skin boils.

Figure 4:
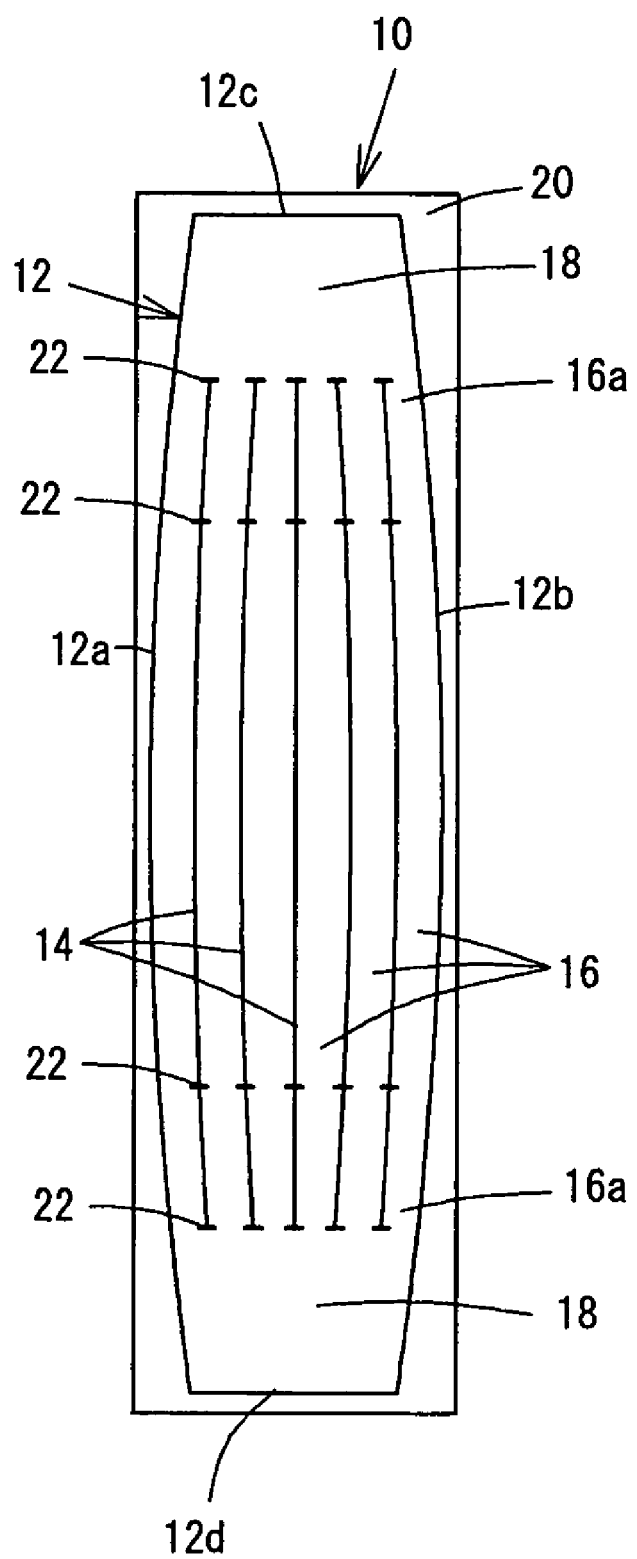
[FIG. 4] A front view of a state where taping tape of another embodiment of this invention is adhered to a peel-away sheet.
Figure 5:
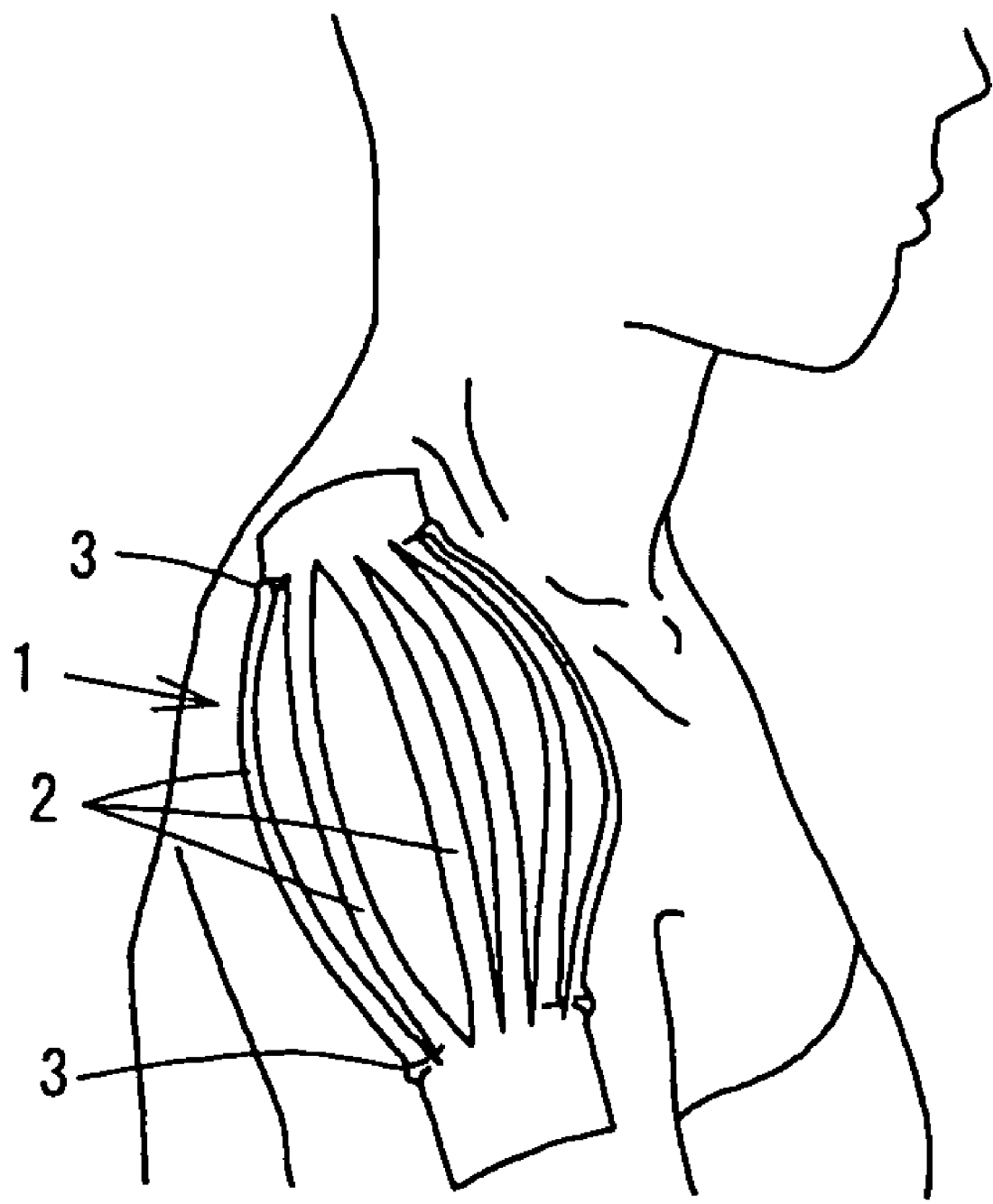
[FIG. 5] A perspective diagram showing a state where taping tape of prior art is used.

The taping tape of this invention is not limited to the preceding embodiment; as shown in FIG. 4, short cuts 22 may also be formed at predetermined intervals in both end portions of the slits 14 and midway along the slits 14 at right angles with respect to the slits 14 in the base material 12. Thus, curvature of the strips 16 when they are adhered to the body is facilitated even more, and the occurrence of wrinkles is controlled.

Further, the size and shape of the taping tape are appropriately changes corresponding to the site to which the taping tape is to be adhered, and the number of the strips is also alterable. The material is also freely alterable as long as it has flexibility and breathability.

The invention claimed is:

1. A taping tape including:
    a base material having elasticity;
    an adhesive layer formed on one side of the base material; and
    plural slits that are formed along one direction on an inner side of the base material and are arranged parallel to each other,
    wherein, without being pulled, both side edge portions of the base material along the slits are formed in curved lines that swell outward and in the vicinities of end portions of the slits are formed obliquely to each other towards a longitudinal direction center of the base material from the vicinities of the end portions of the slits to base material end portions positioned on extensions of the slits, and the slits are formed along the longitudinal direction of the base material and are formed in curved lines along the side edge portions and the end portions of the slits curve towards the center of the base material along the side edge portions.

2. The taping tape of claim 1, wherein short cuts are formed at predetermined intervals in the base material at right angles with respect to the slits.

3. The taping tape of claim 1, wherein the base material comprises a knitted structure.

* * * * *